US00PP31772P3

(12) United States Plant Patent
Larse

(10) Patent No.: US PP31,772 P3
(45) Date of Patent: May 19, 2020

(54) STRAWBERRY PLANT NAMED 'OMAHA'

(50) Latin Name: *Fragaria x ananassa*
Varietal Denomination: Omaha

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 15/998,933

(22) Filed: Aug. 23, 2018

(65) Prior Publication Data

US 2019/0069458 P1 Feb. 28, 2019

Related U.S. Application Data

(60) Provisional application No. 62/550,183, filed on Aug. 25, 2017.

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

*Primary Examiner* — Keith O. Robinson
(74) *Attorney, Agent, or Firm* — Cooley LLP

(57) ABSTRACT

The present invention provides new and distinct strawberry plant designated as 'Omaha' (a.k.a. '109393').

8 Drawing Sheets

Latin name of the genus and species: *Fragaria* x *ananassa.*

Varietal denominations: 'Omaha'.

BACKGROUND OF THE INVENTION

The present invention relates to new and distinct strawberry plant designated as 'Omaha' (a.k.a. '109393').

'Omaha' (a.k.a. '109393') is the result of a controlled-cross between a female parent cultivar designated 'Taia' (U.S. Plant Pat. No. 28,724) and a male parent cultivar designated 'Ginza' (U.S. Plant Pat. No. 23,934) made by the Inventor and was first fruited in Watsonville, Calif. growing fields. Following selection and during testing, the plant was originally designated '109393' and subsequently named 'Omaha'. 'Omaha' is a day-neutral plant.

The new strawberry plant was asexually reproduced via runners (stolons) by the inventor at Watsonville, Calif. Asexual propagules from the original source have been tested in Watsonville growing fields and to a limited extent, grower fields in high elevation. The properties of these plant were found to be transmissible by such asexual reproduction. These plants are stable and reproduce true to type in successive generations of asexual reproduction.

BRIEF SUMMARY OF THE INVENTION

This invention relates to new and distinctive strawberry plant designated as 'Omaha' (a.k.a. '109393'). The plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish strawberry plant 'Omaha' from known strawberry plants. In addition, these plants were confirmed, or will be confirmed to be a unique strawberry germplasm using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used.

DESCRIPTION OF THE DRAWINGS

The accompanying color photographs depict various characteristics of the cultivars as nearly true as possible to make color reproductions.

DETAILED DESCRIPTION OF THE INVENTION

'Omaha' (a.k.a. '109393')

Figure 1A:
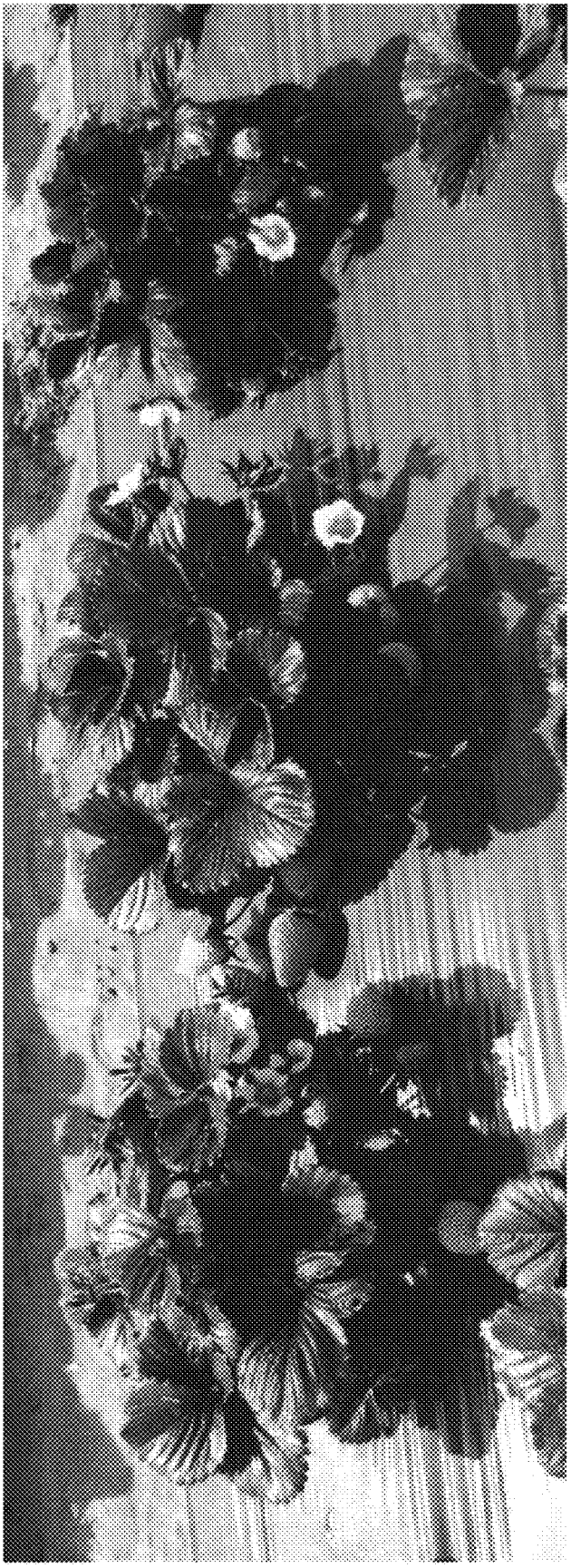
FIG. 1A shows 'Omaha' plant about 6-month old.
Figure 1B:
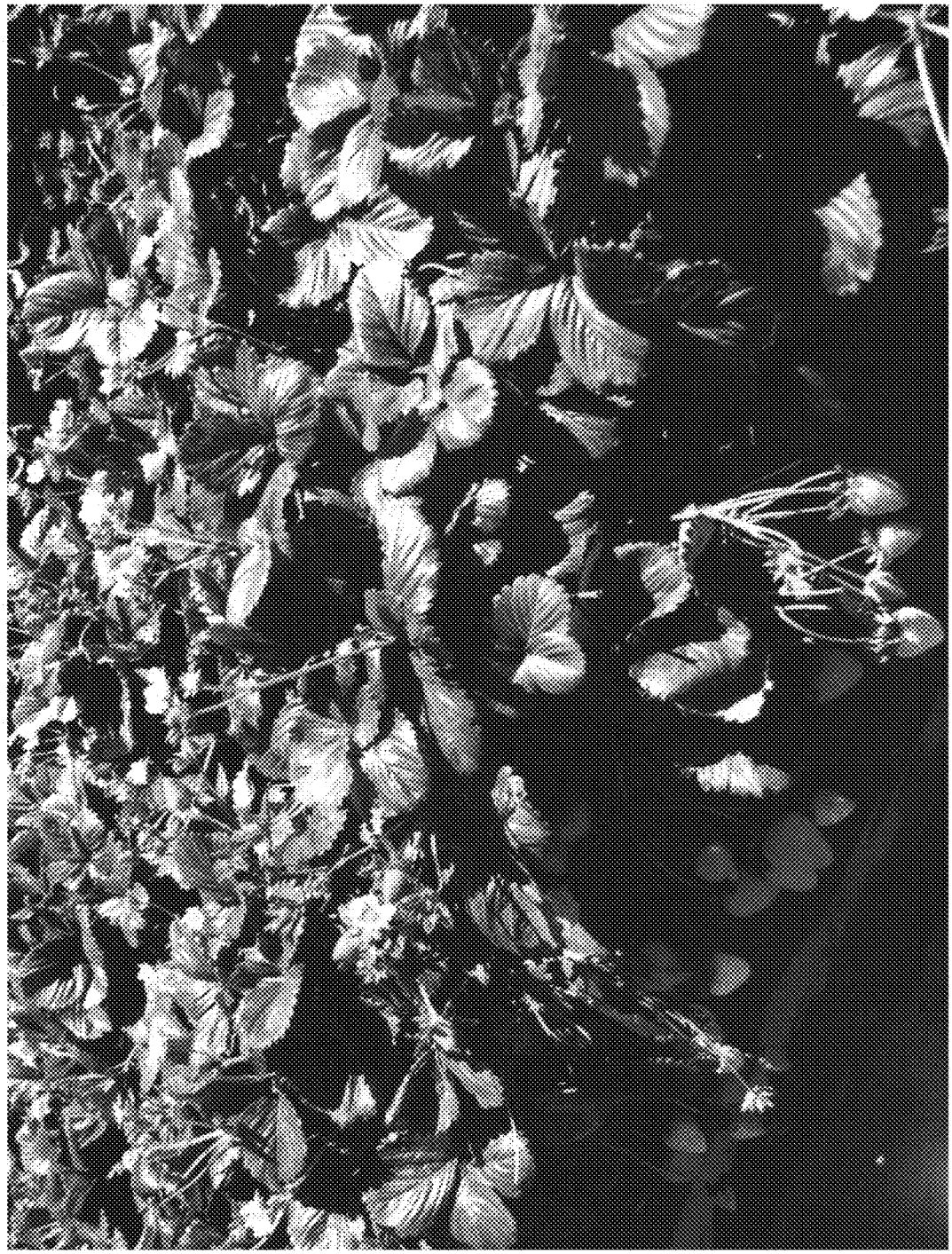
FIG. 1B shows ripe and near-ripe fruits of 'Omaha' about 8-month old.
Figure 1C:
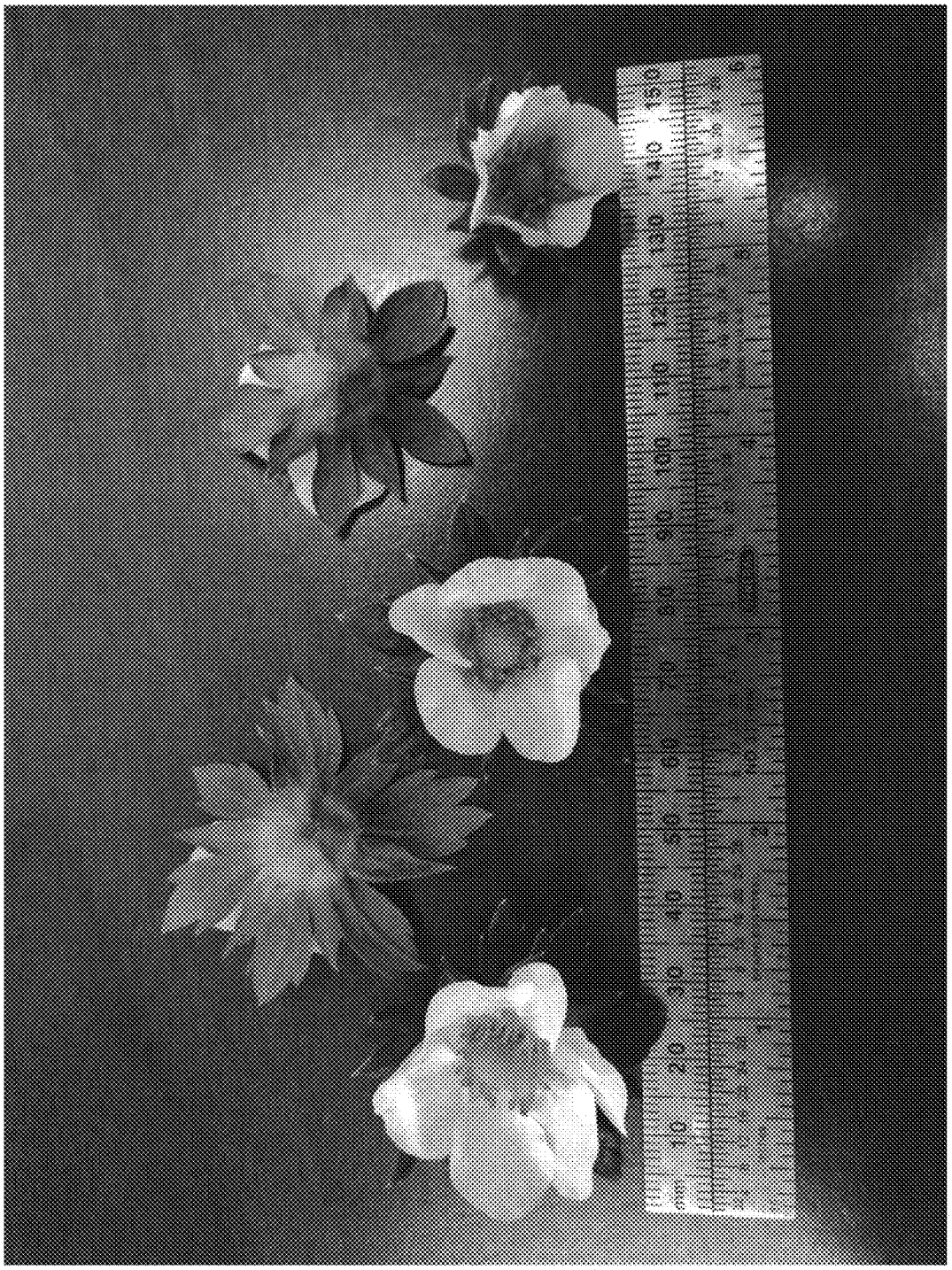
FIG. 1C shows flowers of 'Omaha'.
Figure 1D:
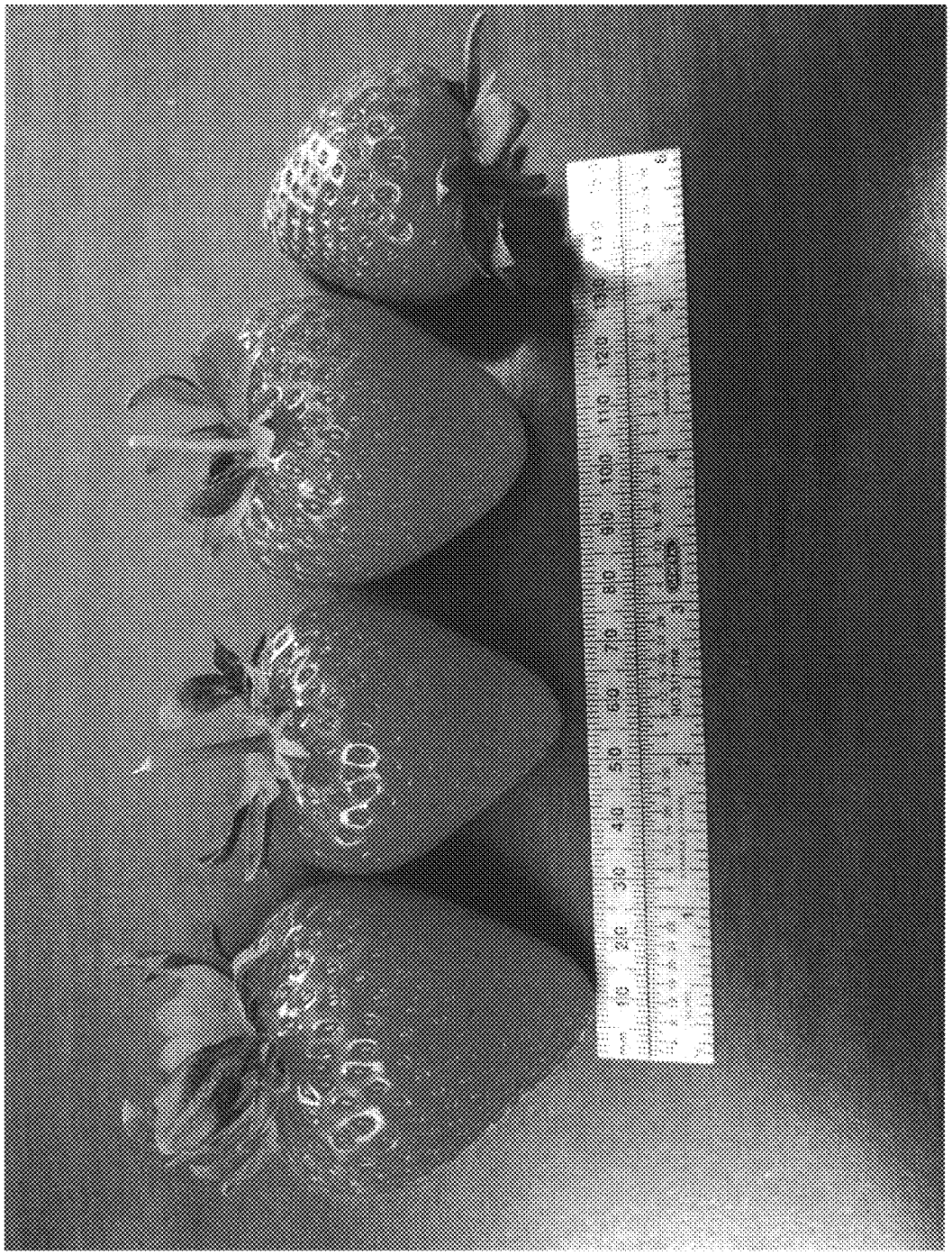
FIG. 1D shows fruits of 'Omaha'.
Figure 1E:
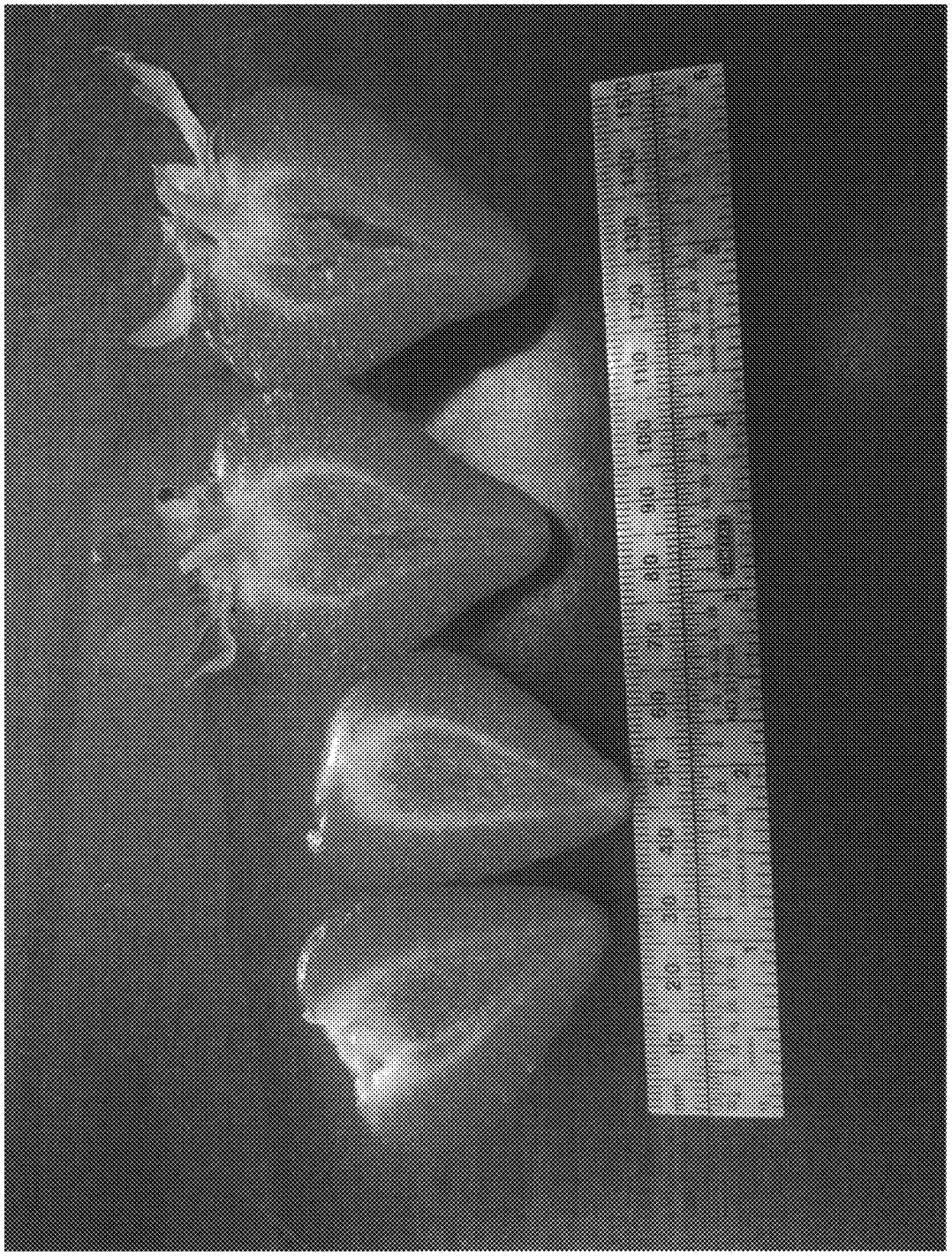
FIG. 1E shows cut fruits of 'Omaha'.
Figure 1F:
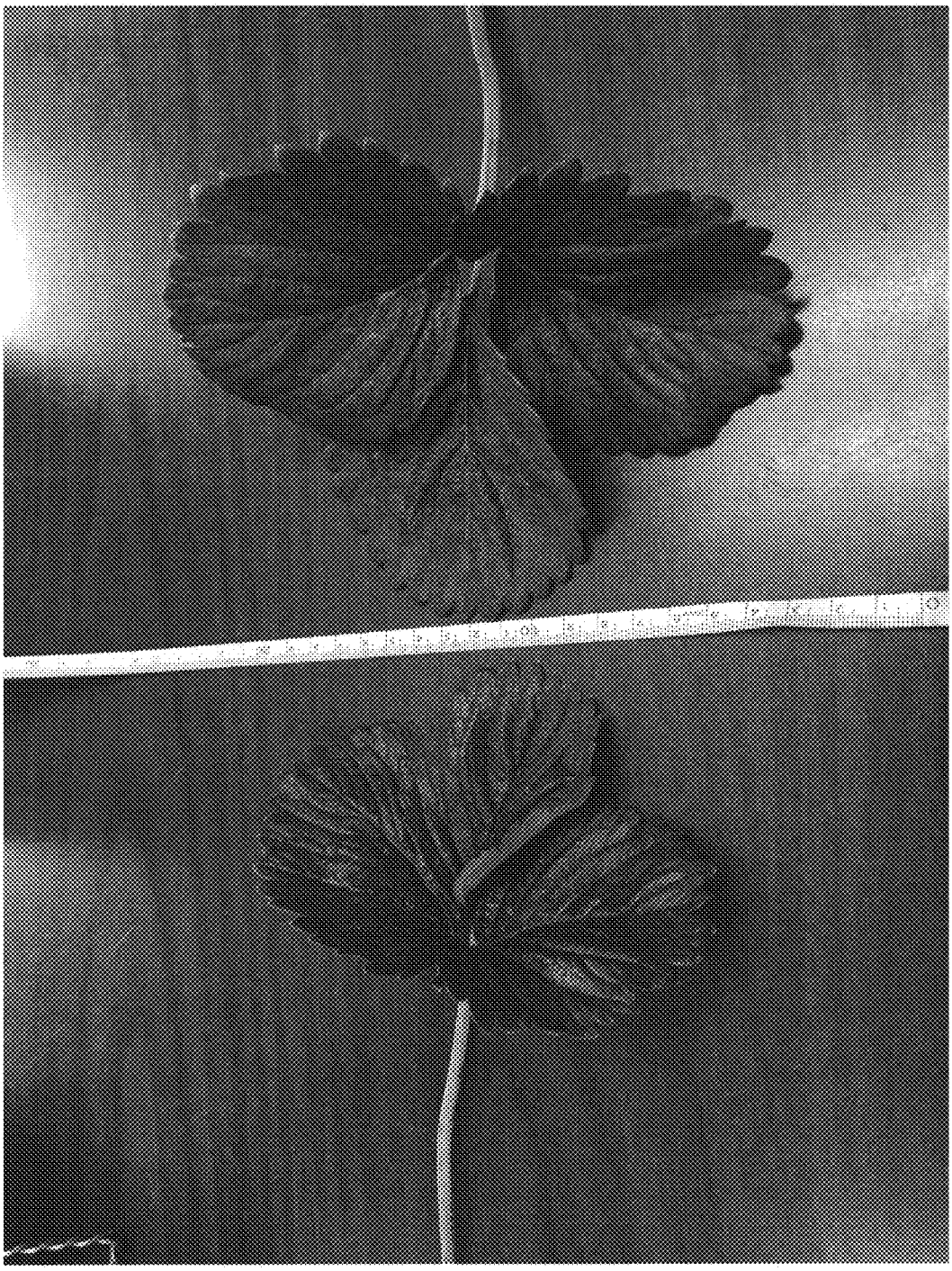
FIG. 1F shows upper leaf of 'Omaha'.
Figure 1G:
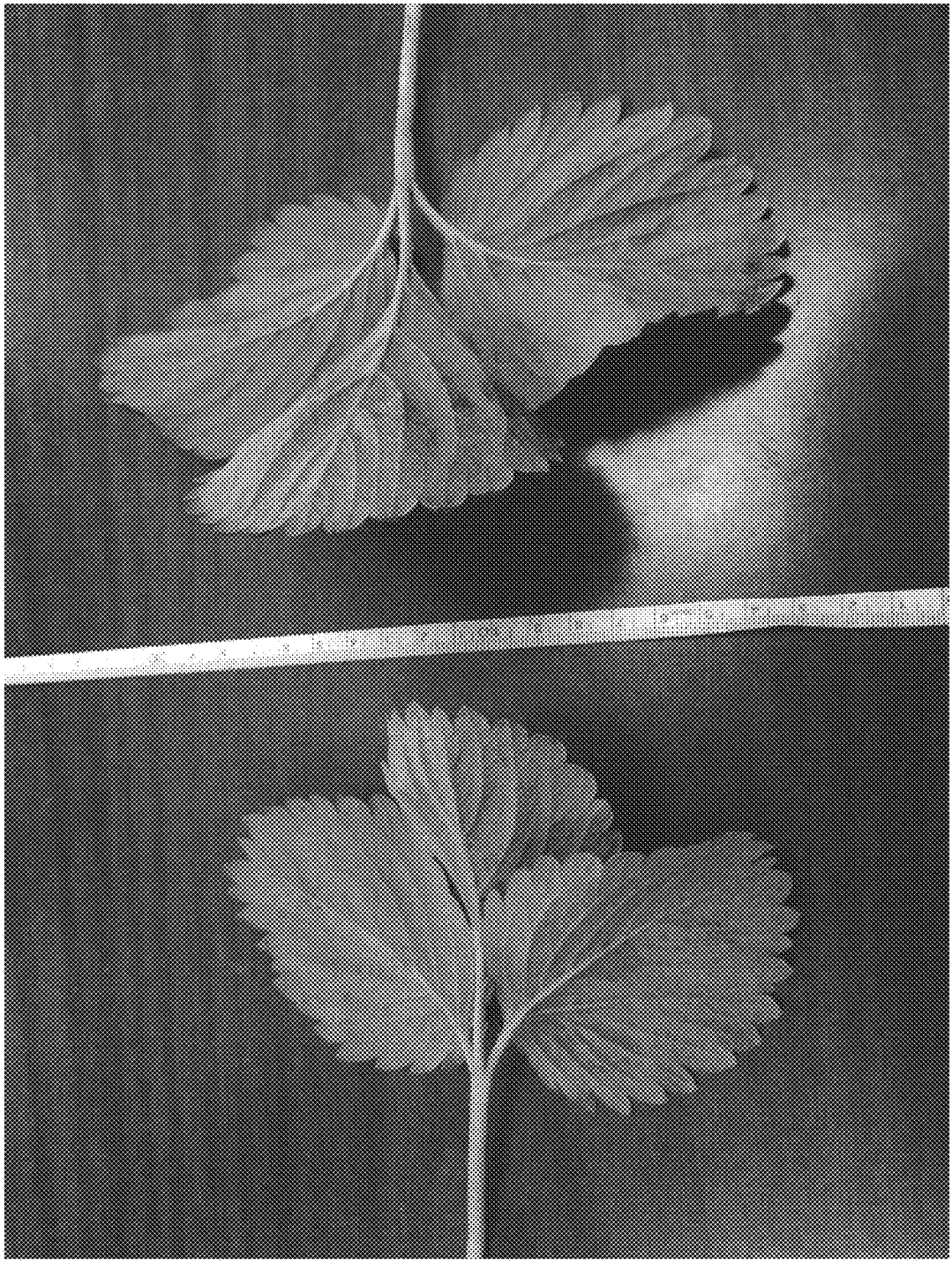
FIG. 1G shows lower leaf of 'Omaha'.
Figure 1H:
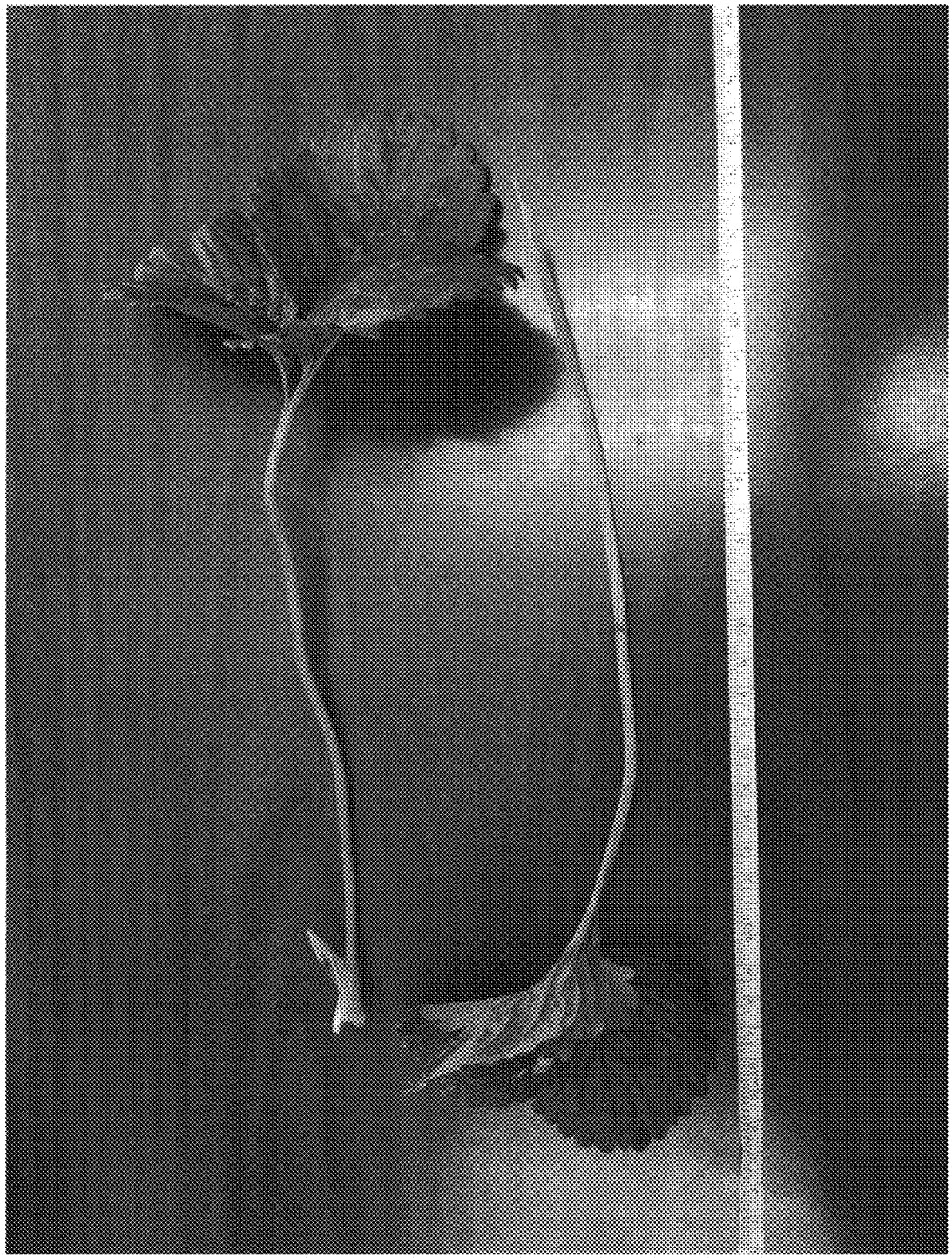
FIG. 1H shows petiole of 'Omaha'.

The following traits and photographs in combination distinguish strawberry variety 'Omaha' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

'Omaha' has not been observed under all possible environmental conditions, and the phenotype may vary significantly with variations in environment. The following observations, measurements, and comparisons describe this plant as grown under normal conditions in Watsonville, Calif. unless otherwise noted. The age of plants when described in Table 1 below is eight months.

TABLE 1

'Omaha' Characteristics

| CharType | Characteristic | 'Omaha' |
|---|---|---|
| General | Plant Habit | annual |
| | Plant Growth Habit | semi-upright |
| | Day length | Day Neutral |
| | Plant Height (cm) | 28 |
| | Plant Width (cm) | 33 |
| | Density of foliage | medium |
| | Plant vigor | moderate to high |
| | Crown diameter (cm) | 3.0 to 4.0 |
| Leaf | Leaflets per Leaf | 3 |
| | Terminal leaflet width (mm) | 8.9 |
| | Terminal leaflet length (mm) | 7.4 |
| | Teeth per terminal leaflet: | 23 |
| | Shape of the terminal leaflet base | acute to obtuse |
| | Shape of terminal leaflet in cross-section | straight to concave |
| | Shape of the terminal leaflet margin | serrate to crenate |
| | Color of upper side of leaflet | 137A |
| | Color of lower side of leaflet | 137C |
| | Leaf blistering | weak |
| | Leaf glossiness | medium |
| | Petiole length (cm) | 20 to 25 |
| | Petiole diameter (mm) | 3.28 |
| Limbs | Petiole color | 145A |
| | Petiolule length (cm) | 1 |
| | Petiolule diameter (mm) | 2.28 |
| | Petiolule Color | 145A |
| | Stipule length (cm) | 2.8 |
| | Stipule width (cm) | 1.1 |
| | Stipule anthocyanin color | 53A |
| | Stipule color (color code) | 145A |
| | Pedicel length (cm) | 9.5 to 16.5 |
| | Pedicel diameter (mm) | 1.34 |
| | Pedicel color (color code) | 145A |
| | attitude of hairs on petiole and pedicel | outwards |
| | Inflorescence position relative to foliage | above |
| | Flower arrangement of petals | touching |
| | Peduncle length (cm) | 16.0 to 29.5 |
| | Peduncle diameter (mm) | 2.67 |
| | Peduncle color (RHS color code) | 145A |
| | Peduncle pubescence | medium |
| Inflorescence | Petal length (cm) | 1.4 |
| | Petal width (cm) | 1.4 |
| | Petal number per flower | 5 to 6 |
| | Upper Petal color | 155C |
| | Lower Petal color | 155C |
| | Calyx diameter (cm) | 4 |
| | Corolla diameter (cm) | 2.75 |
| | Sepal length (cm) | 1.1 to 2.1 |
| | Sepal width (cm) | 0.8 to 1.1 |
| | Time of flowering (50% of plants in bloom) | March |
| | Shape of stigma | capitate |
| | Color of stigma | 6A |
| | Length of style (mm) | 2 |
| | Color of style | 6A |
| | Color of the ovary | 145A |
| | Length of the stamens (mm) | 3 to 5.5 |
| | Number of stamen | 24 to 33 |
| | Shape of anther | dorsifixed |

TABLE 1-continued

'Omaha' Characteristics

| CharType | Characteristic | 'Omaha' |
|---|---|---|
| | Size of anther | small |
| | Anther length (mm) | 0.75 |
| | Shape of anther | dorsifixed |
| | Color of anther | 12A |
| | Amount of pollen | medium |
| | Color of pollen | 4A |
| | Color of filament | 149D |
| | Length of filament (mm) | 2.5 to 5 |
| | Number of flowers per truss | 3 to 6 |
| | Stolon number | 2 to 5 |
| | Stolon anthocyanin | 181A |
| Stolon | Widest diameter of stolon At leaf attachment (mm) | 3.83 |
| | Stolon color | 145A |
| | Stolon length (cm) | 51 |
| | Stolon number | 2 to 5 |
| | Stolon anthocyanin | 181A |
| | Widest diameter of stolon at leaf attachment (mm) | 3.83 |
| | Fruit length (cm) | 40.4 |
| Fruit | Number of fruit per truss | 3 to 4 |
| | Shape difference between primary and secondary fruits | No shape difference |
| | Fruit width (cm) | 30.7 |
| | Fruit skin color | 45A |
| | Fruit flesh color excluding core | 44A |
| | Fruit core color | 41A |
| | Fruit weight (g) | 23.6 |
| | Predominant fruit shape | long conic |
| | Shape difference between primary & secondary fruits | No shape difference |
| | Width of band without of achenes | narrow |
| | Fruit glossiness | medium to strong |
| | Position of achenes | below surface |
| | Achene color | 145A |
| | Achenes per fruit | 273 |
| | Achene weight (g) | 0.19 |
| | Position of calyx | inserted |
| | level of adherence of calyx | medium |
| | Color of calyx | 137A |
| | Firmness of flesh | medium to firm |
| | Evenness of flesh color | even |
| | Sweetness (brix) | 6 to 7 |
| | pH | 3.51 |
| | Yield (g per plant per season) | 2758 |

'Albion' (U.S. Plant Pat. No. 16,228) owned by University of California is a commercial strawberry variety that is similar to, but distinguished from 'Omaha'. The fruit yield of 'Omaha' exceeds the yield of 'Albion' in multiple annual testing cycles performed at the breeders test location in Watsonville Calif. 'Omaha' produces abundant quantities of stolon that must be cut by hand labor in the fruiting field. 'Omaha' does not produce large quantities of stolon (runners) during the fruiting period after propagation in California nurseries and Watsonville fruiting field, which saves labor of about $1,500 per acre because stolon must be removed in order to effect efficient harvest and continued flowering.

Both of the parents of 'Omaha' produce fruit that is lighter in redness coloration than 'Omaha'. One of the parents of 'Omaha', a strawberry plant variety named 'Ginza' (U.S. Plant Pat. No. 23,934) has been observed to have foliage of a lighter green coloration than 'Omaha'. The foliage and plant structure of 'Ginza' is more dense than that of 'Omaha'. The other parent of 'Omaha' is a strawberry plant variety named 'Taia' (U.S. Plant Pat. No. 28,724). The foliage and plant structure of 'Taia' is somewhat more dense than that of 'Omaha'. The foliage and plant structure of 'Omaha' allows better fruit harvest visibility and the canopy can be described as more open than the canopy observed for of each of it's parents. 'Omaha' demonstrated better shelf life, less susceptibility to bruising discoloration and the skin of the fruit of 'Omaha' was observed to better resist abrasion compared to each of it's parents in testing done over multiple weeks of annual fruiting seasons. When 'Omaha' is compared to the male parent, 'Omaha' is a smaller plant. Additionally, 'Omaha' presents fruit with a stronger red color and with a longer fruit shape than the male parent. When 'Omaha' is compared to the female parent, 'Omaha' presents a higher strawberry pH than the strawberries of the female parent. Additionally, 'Omaha' is less dense with foliage and presents fruit with a longer fruit shape than the female parent.

The invention claimed is:

1. A new and distinct cultivar of strawberry plant named 'Omaha' substantially as shown and described herein.

* * * * *